United States Patent
Brodbeck

(10) Patent No.: US 10,568,979 B2
(45) Date of Patent: *Feb. 25, 2020

(54) TREATMENT SYSTEM FOR CLEANING A COMPONENT, IN PARTICULAR AN IMPLANT PART, CONTAMINATED WITH A BIOFILM

(71) Applicant: Zyfoma GmbH, Weiterstadt (DE)

(72) Inventor: Urs Brodbeck, Erlenbach (CH)

(73) Assignee: Zyfoma GmbH, Weiterstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/898,800

(22) Filed: Feb. 19, 2018

(65) Prior Publication Data

US 2018/0169278 A1 Jun. 21, 2018

Related U.S. Application Data

(63) Continuation of application No. 14/765,559, filed as application No. PCT/EP2014/052271 on Feb. 5, 2014, now Pat. No. 9,931,422.

(30) Foreign Application Priority Data

Feb. 5, 2013 (DE) .......... 10 2013 201 884

(51) Int. Cl.
*A61C 17/02* (2006.01)
*A61L 2/03* (2006.01)
(Continued)

(52) U.S. Cl.
CPC ............ *A61L 2/0011* (2013.01); *A61C 17/02* (2013.01); *A61C 17/0202* (2013.01);
(Continued)

(58) Field of Classification Search
CPC ............... A61L 2/035; A61L 2202/21; A61L 2209/134; C25F 1/00; A61C 17/0202; A61C 17/036; A45B 2200/1045
See application file for complete search history.

(56) References Cited

U.S. PATENT DOCUMENTS

| 3,420,760 A | 1/1969 | Bernard |
| 4,337,038 A | 6/1982 | Saito et al. |
| (Continued) | | |

FOREIGN PATENT DOCUMENTS

| CN | 101156975 A | 4/2008 |
| CN | 101400315 A | 4/2009 |
| (Continued) | | |

OTHER PUBLICATIONS

International Search Report received in PCT/EP2014/052270, dated May 12, 2014.
(Continued)

*Primary Examiner* — Steven A. Friday
(74) *Attorney, Agent, or Firm* — Suzannah K. Sundby, Esq.; Canady + Lortz LLP

(57) ABSTRACT

A treatment system (1) for cleaning a component part contaminated with a biofilm, in particular for cleaning bacterially contaminated surfaces of bone implants or dental implants (20), shall enable a particularly effective, locally focused and flexible treatment. For this purpose, the treatment system (1) according to the invention has a conduction element (10), which can be put into electric contact with the component needing treatment and which can be connected to a first pole of an electric supply unit (16), and a media cannula (2) which is provided for supplying a treatment liquid and whose interior is connected in an electrically conductive manner with the second pole of the electric supply unit (16).

6 Claims, 4 Drawing Sheets

Figure 1:
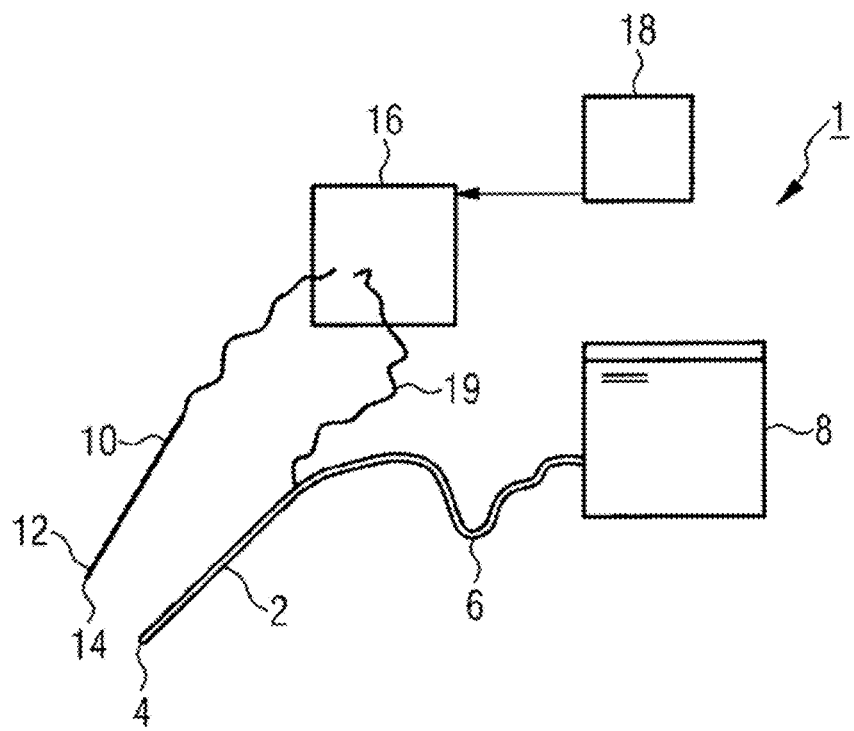

(51) Int. Cl.
*A61L 2/00* (2006.01)
*A61N 1/30* (2006.01)
*C25F 1/00* (2006.01)
*A61C 8/00* (2006.01)
*A61M 37/00* (2006.01)

(52) U.S. Cl.
CPC .............. *A61L 2/035* (2013.01); *A61N 1/306* (2013.01); *C25F 1/00* (2013.01); *A61C 8/0089* (2013.01); *A61L 2202/21* (2013.01); *A61M 2037/0007* (2013.01)

(56) References Cited

U.S. PATENT DOCUMENTS

| | | | |
|---|---|---|---|
| 4,995,540 A * | 2/1991 | Colin .................. | A61C 9/0026 222/132 |
| 5,082,147 A * | 1/1992 | Jacobs .............. | B05C 17/00509 222/137 |
| 5,203,697 A | 4/1993 | Malmin | |
| 5,743,436 A * | 4/1998 | Wilcox ................ | A61C 9/0026 222/137 |
| 5,743,735 A * | 4/1998 | Vollstedt .............. | A61C 1/0076 433/91 |
| 8,668,464 B2 * | 3/2014 | Kensy ................ | A61B 17/3203 417/26 |
| 9,629,699 B2 | 4/2017 | Zipprich | |
| 9,931,422 B2 * | 4/2018 | Brodbeck ............ | A61L 2/0011 |
| 2002/0134797 A1 * | 9/2002 | Grimm ................ | A61C 1/0076 222/205 |
| 2003/0146108 A1 | 8/2003 | Nakamura | |
| 2004/0152041 A1 * | 8/2004 | Metzbower .............. | A61C 5/66 433/90 |
| 2004/0186418 A1 | 9/2004 | Karashima | |
| 2007/0164047 A1 * | 7/2007 | Reidt ................... | A61C 9/0026 222/137 |
| 2008/0086189 A1 | 4/2008 | Taniguchi et al. | |
| 2009/0298010 A1 | 12/2009 | Broyles et al. | |
| 2012/0196251 A1 | 8/2012 | Taft et al. | |
| 2013/0101955 A1 | 4/2013 | Broyles et al. | |
| 2014/0147804 A1 | 5/2014 | Yamamoto et al. | |
| 2015/0076000 A1 | 3/2015 | Ehrensberger et al. | |
| 2015/0282907 A1 | 10/2015 | Zipprich | |
| 2015/0359613 A1 * | 12/2015 | Brodbeck ............ | A61C 8/0013 433/173 |
| 2016/0000947 A1 * | 1/2016 | Brodbeck ............ | A61L 2/0011 205/705 |

FOREIGN PATENT DOCUMENTS

| | | |
|---|---|---|
| CN | 103027757 | 4/2013 |
| DE | 8103191 U1 | 5/1981 |
| DE | 3637887 A1 | 5/1988 |
| DE | 102010017886 A1 | 3/2012 |
| JP | S56-072861 A | 5/1987 |
| JP | H05-285213 A | 11/1993 |
| JP | H08-299999 A | 11/1996 |
| JP | 2008-214591 A | 9/2008 |
| JP | 2009-529377 A | 8/2009 |
| JP | 2016-501057 A | 1/2016 |
| WO | 2003045268 A1 | 6/2003 |
| WO | 2006006923 A1 | 1/2006 |
| WO | 2008011948 A1 | 1/2008 |
| WO | WO2010139762 A1 | 12/2010 |
| WO | 2013012021 A1 | 1/2013 |
| WO | 2013159107 A1 | 10/2013 |

OTHER PUBLICATIONS

International Search Report received in PCT/EP2014/052271, dated May 20, 2014.
International Search Report received in PCT/EP2014/052272, dated May 8, 2014.
First Office Action received in CN 2014800177442 dated Nov. 16, 2016, and received on Mar. 7, 2017.
English Translation of National Preliminary Report on Patentability received in PCT/EP2014/052271, dated Aug. 20, 2015.
Notice of Allowance received in JP 2015-555756, dated Jan. 16, 2018.

\* cited by examiner

TREATMENT SYSTEM FOR CLEANING A COMPONENT, IN PARTICULAR AN IMPLANT PART, CONTAMINATED WITH A BIOFILM

The invention relates to a treatment system for cleaning a component part contaminated with a biofilm, in particular an implant part.

A treatment element, in particular for use with an implant part, as well as a method for cleaning a dental-implant part, are known from the German patent application with the reference number 10 2012 022 593.8, not prior published, whose entire disclosure is incorporated by reference. Such a cleaning of an implant part can be desirable or necessary to guarantee the preservation of the inserted implant in the bone substance. In fact, a biofilm may form on the firm surface of implants, enclosed by tissue and tissue liquid, which biofilm is colonized by bacteria which may finally lead to chronic and recurrent infections. This syndrome is called periimplantitis. In particular in the dental area, similar to parodontitis, a combination of neglected mouth hygiene, adhesion of a biofilm on the usually microrough surface of the post part, and other factors lead to the full picture of periimplantitis, which is characterized by an increasing charge and destruction of the hard and soft tissues. The areas where the hard and/or soft tissues retreat are usually covered by a biofilm.

The cleaning method described in the above-mentioned application is based on the concept, to kill and remove the biofilm or the germs forming the contamination, starting from the implant surface, without damaging the implant surface. For this purpose, an electrolytic process is provided, by which the ions (cations and/or anions) are conveyed by means of electrostatic forces through the biofilm. These ions react chemically or electrochemically on the implant surface. Through these reactions, new compositions of matter are created and/or the ions themselves and/or parts of these ions are converted into the atomic state. Furthermore, it is also possible that the ions react with the surface material (e.g. development of an oxide layer or erosion of material).

The germicidal effect of this process is based on different effects. On the one hand, ions from the biofilm itself (and also from the bacteria) are transported to the anode or cathode through the application of an electric voltage. This may lead to a killing of bacteria and viruses. Furthermore, the ions, while passing through the biofilm, may undergo biochemical reactions, which may also lead to a killing of bacteria and/or viruses. Another possibility of killing consists in that the compositions of matter newly formed on the implant surface possess an antibacterial and/or antiviral and/or antifungal effect. This may, of course, also happen when the ions are converted into the atomic state.

The treatment element described in the above-mentioned application is specifically designed for performing this cleaning method directly on the inserted dental implant, i.e. preferably while the post part is anchored in the bone in the patient's mouth. For this purpose, it is provided to directly connect the treatment element with the inserted post part and to then supply a suitable treatment liquid, which can serve as a basis for the desired electrolytic process when an electric current is applied, in the immediate vicinity of the inserted post part into the afflicted space area of the adjacent bone substance and to charge it with the electric current. The application of this treatment element makes it, however, necessary to establish both a mechanical and an electric contact with the inserted post part. With the construction of the treatment element described in the above-mentioned application, usually the prosthetics at the dental implant and possibly also the latter's abutment have to be temporarily removed for the purpose of fixing the treatment element on the post part.

The present invention is based on the problem to provide an alternative treatment system for cleaning a component part contaminated with a biofilm, in particular an implant part, which enables a particularly simplified handling and a particularly flexible application, in particular without requiring a removal of the prosthetics in case of an implant which is contaminated by a biofilm in a relatively slight manner.

This problem is solved according to the invention by a conduction element which can be put into electric contact with the component needing treatment and which can be connected to a first pole of an electric supply unit, and by a media cannula which is provided for supplying a treatment liquid and whose interior is connected in an electrically conductive manner with the second pole of the electric supply.

Advantageous embodiments of the invention are the subject matter of the dependent claims. Further and/or alternative advantageous embodiments of the invention are also obvious from the description of the figures.

The invention starts out on the consideration that an electrolytic treatment and cleaning of a component covered by a biofilm is made possible in a particularly simple and flexible manner by the fact that the treatment liquid provided as an electrolyte is made available and charged with current by means of components which enable a precisely accurate and localized application. This is possible in a particularly simple manner by a cannula which is electrically conductive on the inside, but electrically insulated on the outside. Inside the cannula, the electrolyte can be guided and also electrically contacted, without having to fear an electric short-circuit with the environment. At the outlet opening of the cannula, the electrolyte can then be supplied purposefully and spatially focused, so that, in this way, the ionic current path for the electrolytic cleaning process can be formed. The second electrode for its part, which, for a purposeful guidance of the current flow, should be formed by the component or implant part to be treated itself, must also be electrically contacted. This can be done by means of a contacting wire, which is preferably designed in the manner of a probe and provided with an electric insulation and which only at its tip is designed in an uninsulated and, therefore, electrically conductive manner. This electrically conductive tip can then be placed directly on the implant surface to be treated or on a component of the prosthetics (e.g. the connecting screw or the abutment, as far as they are electrically conductive). This will then constitute the electron current path.

Via, e.g., a switch, first of all the cleaning electrolyte can be conveyed to the implant surface and then, the energization and, thus, the electrolytic killing and cleaning can be started.

To simplify this process and handling, the ionic current path and the electron current path can be configured in one component, where they can be arranged side by side other or coaxially one inside the other. The coaxial configuration can be designed such that the electron current path is located inside the ionic current path (or vice versa). In a particularly favorable embodiment, a switch, provided for activating the energization, is fixed in the immediate vicinity of the exit of the electron current path. In this case, it is possible to couple the contact pressure force of the exit of the electron current path with the switching action of the start of the electric killing and cleaning process. The end of the electrolytic cleaning cannula/of the exit of the electron current path can be straight or bent. In the variant offered, the exiting direction of the electrolyte can be at an angle of 0° to 180° to the axis of the cannula. To avoid that the electrolyte is pumped into the surrounding tissue at an excessively high pressure, it is possible to mount a reflector and/or a diffusor for the liquid at the exit of the ionic current path. If the electrolytic cleaning cannula is inserted between the implant and soft tissue, the flowing-in of the electrolyte into this pocket might cause an overpressure. To compensate this overpressure, the electrolytic cleaning cannula can be provided on the outside with drain grooves. The electrolytic cleaning cannula can also be used for cleaning hip, knee, shoulder, elbow, foot, tow, hand, finger, vertebral-column implants and/or any other electrically conductive bone implants. The material of the exit of the electric current path is preferably a metal alloy or the same metal as the bone implant to be cleaned. These metals can be: titanium, zirconium, tantalum, and/or alloys of these or other metals, which are used for bone implants. The electric insulation of the two electrodes preferably consists of a biocompatible synthetic material, a glass or a ceramic.

The advantages achieved with the invention consist in particular in the fact that through the combination of the preferably electrode-like conduction element, on the one hand, with the media cannula, which due to the ionic conductibility of the treatment liquid forms a second current path, on the other hand, a reliable removal of the biofilm is possible with high flexibility and high local precision, even from locally limited space areas of the object concerned. For this purpose, the cleaning concept of electrolytic germ killing, recognized as particularly effective, can reliably be applied. Especially in case of an only limited bacterial infestation of the object needing treatment, this cleaning can be effected in a particularly need-based manner, and in case of a treatment of an inserted dental implant, this cleaning can even be effected without having to remove the prosthetics or possibly the abutment.

Figure 2:
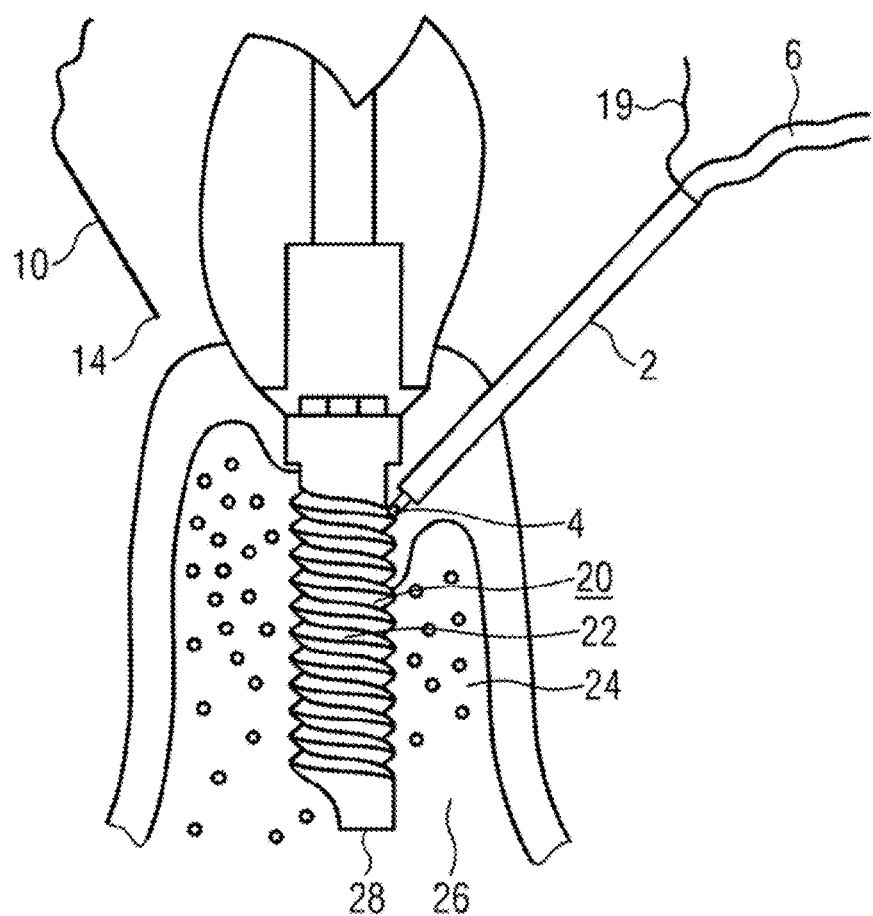
Figure 3:
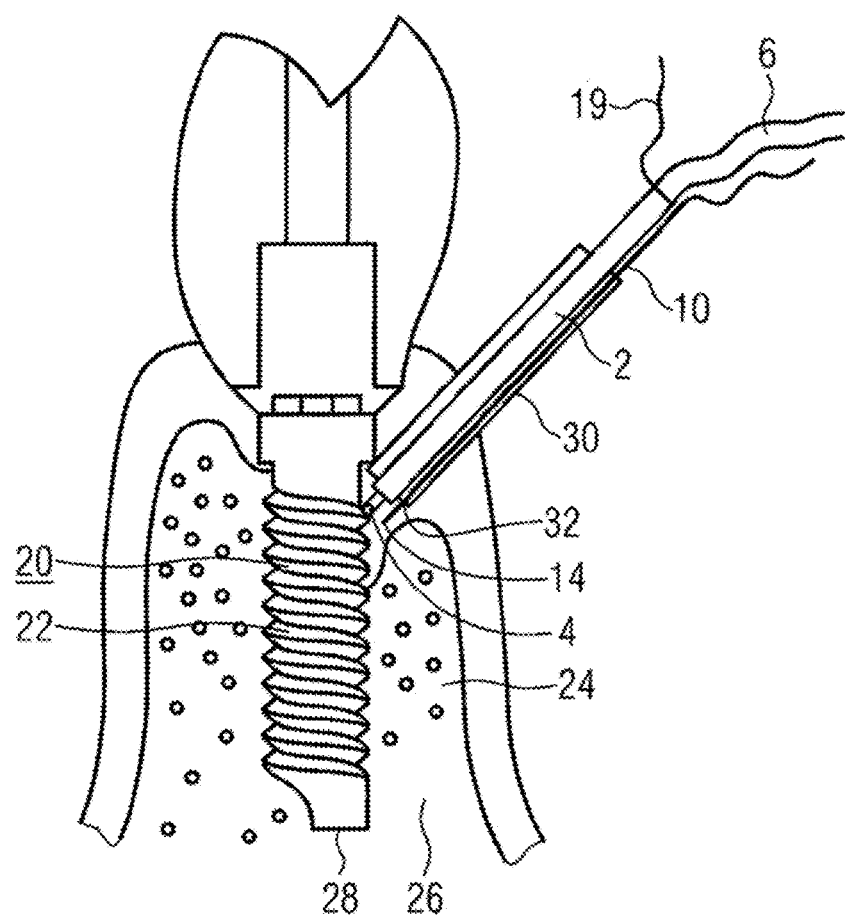
Figure 4:
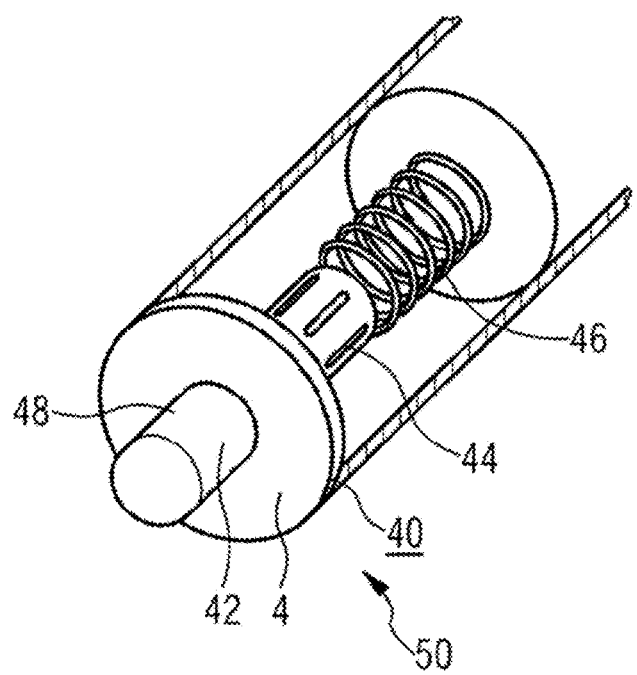

An exemplary embodiment of the invention is explained in detail by means of a drawing, in which FIG. 1 shows a treatment system for cleaning a component contaminated with a biofilm, FIG. 2 is an enlarged detail of the treatment system of FIG. 1, FIG. 3 is an enlarged detail of an alternative embodiment of the treatment system of FIG. 1, and FIG. 4 is an enlarged detail of the outlet area of a media cannula.

Identical parts are marked with the same reference numbers in all figures.

The treatment system 1 according to FIG. 1 is provided for cleaning a component part contaminated with a biofilm, in particular an implant part. The treatment system 1 is designed for an electrolytic cleaning concept, in which the component needing treatment is charged, in a purposeful and localized manner, with a specific, suitably chosen treatment liquid and then, a current flow through the component needing treatment and the treatment liquid is generated. For this purpose, the treatment system 1 comprises a media cannula 2, in which the treatment liquid is carried and can be supplied via an outlet opening 4. The end area of the media cannula 2 is of an elongated design, so that a purposefully localized and controlled supply of the treatment liquid is possible. On the media side, the media cannula 2 is connected via a connection hose 6 with a reservoir 8 for the treatment liquid.

In addition, the treatment system 1 is specifically configured as an electric system. As a design principle, it is in particular provided to enable a pulsed charging of the medium carried in the media cannula 2, in particular of the treatment liquid carried therein, with current impulses. The treatment system 1 is configured according to the design principle that the electric current can be fed to the component needing treatment and that the latter can be used as an electrode. For this purpose, the treatment system 1 comprises a conduction element 10 forming an electric current path. In the exemplary embodiment, said conduction element 10 is designed in the manner of a "conventional" electrode, i.e. in particular as an electrically conductive needle-like element made of metal, but can also consist of any other conductive material. The outsides of the conduction element 10 are provided with an electric insulation and has only at its free end 12 an exposed metallic contact tip 14. In operation, the latter can suitably be pressed against the component needing treatment, thus establishing an electric contact with said component. Electrically, the conduction element 10 is connected with one of the poles of an electric supply unit 16, in particular a current or voltage source.

The electric supply unit 16 is associated with a control unit 18, via which the current supplied or the voltage supplied can be controlled and adjusted. In addition, the control unit also acts upon a conveying system, not shown in detail, of the connection hose 6, with which the flow rate of the treatment liquid through the connection hose 6 can be adjusted.

To form an opposite pole or the counterelectrode, it is provided to utilize the electric conductivity of the treatment liquid carried in the media cannula 2. For this purpose, the interior of the media cannula 2 is, for its part, electrically connected, via a cable 19 which is connected with the interior of the media cannula 2 in an electrically conductive manner, with the other pole of the electric supply unit 16. Thus, the outlet opening 4 of the media cannula 2 forms in electric terms a contact or an electric contact point, via which the current flow into the component needing treatment is effected. By suitably positioning the media cannula 2 and its outlet opening 4, if possible, in the immediate vicinity of the component needing treatment and by using the outlet opening as an electric contact, it is achieved that the electric current applied for the purpose of treatment and cleaning can flow through the surface zone of the component needing treatment, afflicted by the bacteria, and, from there, as directly as possible, i.e. in particular without making any "detours" through further body tissue or the like, to the outlet opening 4 serving as a contact surface. Therefore, the media cannula 2, inclusive of the electrically conductive treatment liquid carried therein and the corresponding connection elements, form in the exemplary embodiment a second conduction element, forming an electric current path to the outlet opening 4.

The media cannula 2 is made of a suitably chosen electrically insulating basic material, for example, a synthetic material. In order to further promote the utilization of the treatment liquid present in the media cannula 2 as an electric conduction element and to guarantee in particular a reliable electric contacting, the inside of the media cannula 2, i.e. the inner surface facing towards the treatment liquid, is, however, provided with an electrically conductive coating.

As can be seen from the enlarged representation according to FIG. 2, the media cannula 2 is designed for feeding the treatment liquid to the component needing treatment in a purposeful and localized manner. In the exemplary embodiment, this is explained by means of a dental implant 20 inserted into a patient's mouth bone; but, of course, other applications are also imaginable, in which a component, for example a bone implant of any construction, shall be cleaned in a flexible and focused manner from the contamination with a biofilm. FIG. 2 also shows a spatially limited space area 24, adjacent to the dental implant 20 in the area of its external thread 22, in the jawbone 26, which is afflicted by periimplantits and correspondingly infested with bacteria.

In general, dental-implant systems, in particular also two-part implant systems, present the problem that inflammations or inflammation focuses may arise due to a penetration of bacteria or germs into the tissue area near the place of insertion, in particular in the area of the external thread 22 cut into the jaw. Such inflammations, in particular also as a consequence of a so-called periimplantitis, may lead to a serious deterioration of the tissue and the bone in the area of the place of insertion, especially when they are able to develop and take hold over a long period. Without suitable countermeasures, these deteriorations may lead to the necessity to remove the entire implant system from the bone and replace it by another prosthetics. This most undesirable effect caused by the periimplantitis may, therefore, lead to a total loss of the implant system, so that renewed surgical measures, such as, for example, scraping out the afflicted area in the jawbone and treatment with a new implant system might become necessary. Such a removal may, furthermore, entail a loss of bone or other loss of tissue substance, which in the extreme case may even make a new treatment with another implant completely impossible. Such a necessity of a new treatment caused by a periimplantitis may occur even after relatively long periods after the first insertion of the implant system of, for example, up to several years or even decades.

The germs or bacteria observed in connection with a periimplantitis may in principle colonize the inside of the components of the dental implant 20, but, as a rule, they preferably adhere directly on the surface of the dental implant 20 inserted into the jawbone 26, in the contact area with the surrounding tissue or bone material, i.e. in particular in the area of the external thread 22. In the area of the latter, the surface of the dental implant 20 can be provided with a roughening or the like, in order to particularly promote the growing-in of the tissue or the bone and to support the healing-in of the dental implant 20 after its insertion. Especially in the area of such a roughening of the surface, actually considered as particularly favorable for the implant system, however, the colonization of germs or bacteria may take place increasedly, the roughness making a specific removal of the existing germs or bacteria even more difficult.

Therefore, suitable countermeasures are urgently required, in order to be able, in case of a beginning or already existing periimplantitis and under preservation of the already inserted implant system, to efficiently combat the inflammation focus and to kill the germs that have penetrated, so that afterwards, sound tissue or sound bone substance can develop again in the area around the external thread 22. For this purpose, it is desirable, in addition to a specific killing of the germs or bacteria in the afflicted area, to also reliably remove their material residues and fragments from the space area concerned, so that then, the afflicted area can be filled again by sound tissue or bone material and an intimate connection between the outer surface of the dental implant 20 and the surrounding tissue or bone material can develop again. In addition, the biofilm formed by the bacteria layer, including the organic residues of killed bacteria, should reliably be removed.

For this purpose, i.e. for killing germs or bacteria in the insertion area of the dental implant 20 and in particular also for subsequently rinsing, removing and carrying away the residues of tissue and material of the killed bacteria, the treatment element 1 is provided. With regard to its design and fundamental configuration, the treatment element 1 is based on two main concepts, each of which is independently considered as inventive: on the one hand, it is designed for specifically killing the germs or bacteria present in the insertion area of the dental implant 20 through specifically feeding a cleansing agent or disinfectant which is bactericidal, but tolerated by the human organism. On the other hand, it is designed for removing any residues or fragments of germs and/or bacteria still adhering on the surface of the dental implant 20, in particular in the area of the external thread 22, through a suitable charging with current or current impulses, from the outer surface of the dental implant 20, so that such residues can then be washed out.

In a first aspect, which is independently considered as inventive both with regard to the configuration of the system and with regard to the provided steps of the treatment method, the treatment system 1 is, therefore, designed, both structurally and functionally/conceptually, for specifically feeding the treatment liquid for killing the germs or bacteria and/or for cleaning the inserted implant part into the insertion area of the dental implant 20, in particular the area of the latter's external thread 22.

In a second aspect, which is also independently inventive both with regard to the configuration of the system and the choice and composition of the basic constituents of the utilized treatment liquid and with regard to the provided steps of the treatment method, the treatment system 1 is designed for reliably detaching the killed bacteria or germs, respectively their residues or fragments, from the outer surface of the dental implant 20, so that they can then be washed out and, afterwards, sound tissue or bone material can again get into contact with the surface of the dental implant 20 and the latter can again grow completely into sound tissue or bone material. For detaching the bacteria or germs, respectively their residues or fragments, from the surface, it is provided to wet the latter with a conductive treatment liquid, charging it with pulsed current impulses. It has also turned out most surprisingly that exactly this pulsed charging with current impulses, in combination with suitably chosen ion concentrations in the treatment liquid, seems to effect the detachment of the bacteria or germs, respectively their residues or fragments, from the surface underneath in a particularly reliable manner, even if said surface is roughened and, in fact, particularly promotes the adhesion of organic material due to its surface structure.

This is based on the surprising discovery that the charging of the dental implant 20, and in particular of its post part 28, with current, using a suitably chosen treatment liquid, in the area of the outer surface of the post part 28, i.e. in particular in the area of the external thread 22, leads to an electrolytic reaction in the treatment liquid and, thus, possibly to the generation of gas bubbles in the immediate vicinity of the surface. Through this formation of gas bubbles on the surface of the post part 28, the superficially adhering components or fragments of the germs or bacteria are also detached and completely removed, so that they cannot offer a basis or a nutrient medium for a new colonization of germs in these areas. What remains is a roughened and porous surface, cleaned from germs, bacteria or their components or residues, of the post part 28, which can serve well as a basis for a future integration into the regrowing bone tissue. The remaining surface can also be formed by a titanium-oxide layer, which would also arise when anodizing the surface.

A particular promotion of this separation of superficially adhering biofilm components from the inserted post part 28, which is desirable in the sense of a reliable cleaning of the surface, can be achieved through an advantageous, particularly well suited process guidance during the charging with current. Said process guidance can be such that due to the current flow, an electrolytic formation of gas bubbles taking place in the area of the inserted surface is particularly increased. Here, the post part 28 can be switched anodically or cathodically. In particular in case of an at least temporary cathodic switching of the post part 28, hydrogen gas, which contributes in a particularly efficient manner to the formation of gas bubbles, develops through electrolytic induction, whereas, in case of an anodic switching of the post part, depending on the composition of the treatment liquid, chlorine gas, oxygen, nitrogen, carbon monoxide and/or carbon dioxide develop. The gas bubbles forming thereby rise in the surrounding liquid and thus generate entraining effects, through which the above-mentioned surface components are also removed and discharged towards the outside. It was, for example, most surprisingly observed that, when using a solution containing positive ions, for example, an aqueous saline solution, these ions deposit on the post part 28 when the latter is cathodically switched and, thus, clearly increase the formation of gas bubbles. For example, the presence of $Na^+$ ions in case of a cathodic switching of the post part 28 leads to a considerable formation of gas bubbles, because $Na^+$ reacts at the cathode with the surrounding water and forms NaOH, releasing hydrogen.

In a third independent inventive aspect, also both with regard to the configuration of the system and with regard to the provided steps of the treatment method, the treatment system 1 is designed for a particularly simple and efficient combination of the before-mentioned aspects. This is based on the concept that both the provided feeding of the cleaning liquid and the specific detachment of the residues and fragments of bacteria and germs can be achieved by applying the above-mentioned current impulses in a common system and, thus, with particularly simple means.

The treatment liquid used is suitably chosen and composed in view of these aspects. Choice and composition of the basic constituents of the treatment liquid are chosen in particular in view of the intended function, i.e. application of an electric current in the space area of the surface needing treatment, it being in particular ensured that the electric conductivity of the treatment liquid is sufficiently high for this purpose. This shall be ensured in particular by a chosen sufficiently high ion density in the treatment liquid. For this purpose, a metallic salt, preferably in aqueous solution, is provided as a basic constituent of the treatment liquid. Said metallic salt supplies the ions for the transport of current and, in addition, the conversion products arising after the respective electrode reaction can also posses suitable biochemical effects. By specifically choosing a sufficiently high electric conductivity, it shall be ensured that during the performance of the cleaning method at the inserted implant the current flows through the treatment liquid and, thus, through the parts and components needing treatment, but not through the patient's body tissue, so that a risk for the patient through an unwanted current flow through soft tissue, bones, blood, and/or other body materials can be minimized. The electric conductivity of the treatment liquid should, if possible, amount to a multiple of the electric conductivity of blood, bones, soft tissue, fatty tissue, or other body materials.

Consequently, the following conductivity values are in particular taken into consideration in the choice and composition of the basic constituents of the treatment liquid (the electric conductivity a being indicated in the usual unit mS/cm):
Skin: 0.03-0.1 mS/cm
Bone: 0.06-0.2 mS/cm
Fatty tissue: 0.20-1.0 mS/cm
Muscular tissue: 0.80-2.5 mS/cm
Blood: approx. 6.7 mS/cm
Other body liquids: approx. 15 mS/cm To keep the risk potential for the patient suitably low and to restrict the current flow to the desired regions, the electric conductivity should, therefore, amount to at least twice, preferably five times, particularly preferably ten times the conductivity of other body liquids. Therefore, the electric conductivity of the treatment liquid should have a value of at least 30 mS/cm, preferably at least 75 mS/cm and particularly preferably at least 150 mS/cm. In comparison with blood, this means that the electric conductivity of the treatment liquid preferably amounts to at least approx. five times, preferably at least approx. ten times and particularly preferably at least approx. twenty times the conductivity of blood. Measurements have shown that, when applying a treatment liquid chosen in this way, the electric voltage to which the body tissue, the blood, the body liquids, etc. are exposed, is lower than 6 V, preferably lower than 3 V, particularly preferably lower than 1.5 V, so that damages for the patient can securely be excluded, as the voltages are kept low. To achieve such a conductivity, in particular the ion concentration in the treatment liquid and in the basic constituents forming the latter are chosen sufficiently high; for this purpose, caustic solutions, acids, salts, and/or other ion-forming substances or compositions of matter can be used.

Choice and composition of the basic constituents of the treatment liquid take into consideration to a particularly high degree that the cleaning or biofilm-detaching effect of the electrolytic treatment of a contaminated implant surface is based on a combination of several causes, which should be made use of, if possible, complementarily to each other. On the one hand, gases or gas bubbles may form, when the current flows through the electrolyte, preferably in the area of the electrodes, which gases or gas bubbles have a detaching (mechanical) effect on the biofilm. These gases develop immediately at the implant surface serving as an electrode and, thus, between said implant surface and the biofilm. The growth rate and maximum size of the developing gas bubbles influence the detachment process.

The second reason for the implant-cleaning or biofilm-detaching effect of the electrolytic process is the decomposing, destroying, and dissolving effect of the electrolytically created substances or compositions of matter on the adhesion of the biofilm on the implant surface, i.e. on the gluing or anchoring mechanism.

The third reason for the cleaning or detaching effect of the electrolytic process is based on material-eroding effects of the implant material, through which component parts or particles of the implant properly speaking are extracted therefrom in its surface area.

The fourth reason for the cleaning or detaching effect of the electrolytic process is based on the formation of an oxide layer of metallic implants, which allow this. In this case, metal atoms of the metallic basic material penetrate the possibly already existing oxide layer due to the applied electric voltage and react with substances of the electrolyte (mostly oxygen=>formation of metal oxide). In metals which do not form an oxide layer or do not form a mechanically stable oxide layer, non-oxidic compositions of matter (mostly salts) may also arise, which then get into solution.

The basic constituents provided for forming the treatment liquid are suitably chosen and combined with each other in view of these effects. Furthermore, it is taken into account as a fundamental design target that no toxic effects or effects which are hazardous or disagreeable to a patient in another manner should occur, so that the treatment liquid is also suitably for being applied on the inserted dental implant, i.e. in the patient's mouth. In the exemplary embodiment, the basic constituents provided are at least one salt, on the one hand, and one acid, on the other hand, preferably diluted with water, whose choice and composition depends in particular on the above-mentioned criteria. It is particularly preferable to provide, as an acid, phosphoric acid, citric acid, formic acid, ethanoic acid, lactic acid, carbonic acid, or a combination thereof. Alternatively or additionally, it is particularly preferable to provide, as a salt, sodium, calcium, aluminium, magnesium, tin, or potassium iodide, chloride, nitrate, carbonate, or hydrogen carbonate, and/or ammonium chlorite, nitrate, or iodide, or a combination thereof.

Furthermore, it is taken into account that the provided electrolytic process can be guided, at choice, with anodic or with cathodic switching of the dental implant. Consequently, a difference is made in the following between an anodic reaction and a cathodic reaction.

In an anodic reaction, i.e. in case of an anodic switching of the dental implant 20, the anions present in the treatment liquid are oxidized on the anode, in general through the extraction of electrons. This may lead to an immediate reaction with the material, in particular to the formation of an oxide layer and/or of a salt, with the implant material. Bone implants and, thus, also the dental implant 20, mostly consist of titanium, zirconium, tantalum, or alloys of these metals. Furthermore, other metals are added by alloying. These metals or metal alloys possess in most cases a high degree of oxide-layer formation. This oxide-layer formation has a passivating effect on the surface, with the consequence that the anodic reaction of these metals or metal alloys is prevented or at least very greatly reduced. As in most cases, compositions of matter with oxygen are found in the biofilm, it is in most cases not possible to prevent this passivation. If the dental implant is switched anodically, the detaching and cleaning effect is, therefore, in most cases limited to the oxide-layer formation. It could be shown in extensive examinations that with higher operating voltages of, for example, more than 20 V, a material-eroding process is possible, but that the latter entails a strong heat development. This heat development may lead to an undesired necrosis of the bone. Furthermore, the material erosion resulting therefrom changes the properties of the original implant surface in an unwanted manner.

It has surprisingly turned out that, as an exception thereto, a basic material of the post part 28 containing aluminium as an alloy component (for example, titanium grade V, containing approx. 6% aluminium and 4% vanadium) enables an anodic energization of the post part 28, without the formation of an oxide layer excessively impeding the process. In this way, it is possible, depending on the composition of the treatment liquid, to generate chlorine or iodine gas or else $CO_2$ directly on the surface of the post part 28 and, thus, make it immediately usable for the intended detachment of the biofilm. For such a process guidance, the treatment system 1 is particularly advantageously provided with a conductive surface coating, for example made of DLC ("diamond-like carbon"), a metal or a conductive synthetic material.

For the above-mentioned reasons, the post part 28 is, however, in general preferably switched cathodically during the treatment with the treatment liquid. In this case, positively charged ions (cations) wander to the surface of the dental implant 20. These ions can be in particular $H^+$ ions, metal ions or long-chain hydrocarbon ions, e.g. from ionic liquids. The salt provided as a basic constituent for the treatment liquid is in this case particularly purposefully chosen in view of the properties of the cations which shall promote the above-mentioned process or make it possible in the first place. To generate as high an electric conductivity as possible, small ions ($H^+$ ions or metal cations) are particularly suitable, which, in addition, in the manner of another particularly favorable effect, are able, in a relatively easy manner, to penetrate the possibly existing biofilm. $H^+$ ions are reduced to elementary hydrogen H on the cathode formed by the dental implant 20. This generates a formation of bubbles.

Alkali metals, alkaline earth metals and/or aluminium react on the cathode with the surrounding water and form elementary hydrogen and its metal cations and $OH^-$ ions. This means that hydrogen bubbles and the hydroxide of the used metal ions form. Through the combination of these components, it is, therefore, achieved, in addition to the detaching effect of the arising hydrogen, that the metal hydroxide has an antibacterial effect and a diluting or dissolving influence on the biofilm or the latter's adhesion mechanism.

To avoid incompatibilities with the body tissue, in particular the metal cations produced naturally in the body (e.g. potassium and/or sodium ions) are particularly preferred as metal cations. Furthermore, calcium, magnesium and/or aluminium ions are also suitable. The salt provided as a basic constituent for the treatment liquid is, therefore, particularly preferably a salt of these metals, in particular because these metal cations can anyhow exclusively be made available in the form of a salt, e.g. dissolved in water.

These metallic salts can be compounds of the above-mentioned metals with a suitable halogen, for example with sulphur, phosphor, nitrogen, fluorine, chlorine, iodine, bromine, hydrocarbon, oxygen, boron, or other nonmetals. The halogen is advantageously suitably chosen considering the principle "the larger the anion, the lower the electric conductivity" and in view of the generally desired high electric conductivity. Furthermore, preferably only substances influencing neither health nor the periimplantary tissue are taken into consideration as anion. Furthermore, it has to be taken into account that disagreeable smells or taste compounds are unwanted. For these reasons, sulphur anions or anions containing sulphur in combination with oxygen or other elements are considered as rather unsuitable. This also applies to fluorine, bromine, nitrogen, and boron ions, possibly also in combination with other elements.

In contrast to that, phosphates, phosphate ions and hydrogen phosphate ions mostly have hardly any detrimental effect or none at all. Chlorine ions or ions containing chlorine mostly have an antibacterial effect. Should the chlorine ion, however, be electrolytically oxided and be present in water in the elementary state, hydrochloric acid and hypochlorous acid will form. It is true that, in combination with the cathodically generated hydroxide, this would lead to a neutralization, but examinations have shown that the chlorine arising on the counterelectrode to the implant (anode) escapes from the electrolyte to a great extent in the form of gas. If it is not possible to suck off the chlorine completely during the treatment, severe cauterizations in the lungs and/or the mucous membranes may result. In this case, one has to balance whether the benefit for the patient or the latter's endangerment is greater.

With regard to the phosphates of aluminium, potassium, sodium, calcium, or magnesium, it must, furthermore, be noted that their dissolubility in water is so low that a sufficient electric conductivity of the electrolyte is not guaranteed (these phosphates are, however, very well suited as additives of the electrolyte for buffering the pH-value). Although chlorides of the four above-mentioned metals would have a sufficient dissolubility in water and a good cleaning and killing effect on the biofilm, they cannot be considered as the optimum. In case of nitrates and/or nitrites, an endangerment of the patient through the formation of $NO_x$ gases has to be expected. For this reason, the use of nitrites or nitrates is not advisable.

In view of the above-mentioned design targets, in particular for a particularly good compatibility for the patient, iodine is provided in a preferred embodiment as halogen. It is particularly advantageous that iodine salts of potassium and of sodium are naturally present in the human body. Through the oxidation of iodine ions on the anode, first of all elementary iodine develops, which can dissolve in a sodium-iodide/potassium-iodide solution. An iodine-potassium-iodide solution or an iodine-sodium-iodide solution will result thereby. Both solutions are strong disinfectants, which have proved themselves in human medicine.

Pure solutions of sodium iodide or potassium iodide or a mixture of the two entail, however, the possible disadvantage of the formation of sodium hydroxide and/or potassium hydroxide and the resulting increase of the pH-value. It could, in fact, quite generally, be considered as a problem of the above-mentioned formation of metal hydroxide that a metal hydroxide increases the pH-value of the electrolyte. Such an increased pH-value and the developing caustic solution of the dissolved metal hydroxide might have an undesired influence on the surrounding tissue in the patient's mouth and in particular, on the bone. Furthermore, adjacent teeth might be damaged. Furthermore, the formation of hydroxides might lead to their precipitation on the post part 28 or generally on the component part needing treatment, due to their very low water solubility, thus impeding the further current flow and, thus, the process as a whole. At best when using a calcium salt in the treatment liquid, the developing calcium hydroxide, which is present in the bone material, could be integrated into the bone; calcium is, therefore, a particularly preferable constituent of the salt. To compensate these undesired influences, the treatment liquid contains the acid as another basic constituent in the manner of a pH-buffer or pH-reducer.

The acid, for its part, is chosen, in the manner of a design criterion, in such a way that it does not endanger, if possible, the patient or the periimplantary tissue, but, on the one hand, neutralizes the hydroxide (and prevents, if possible, an increase of the pH-value to more than 7), whereby, on the other hand, the reaction products should serve for the actual target of cleaning the implant body and removing the biofilm. As mineral acids, phosphoric acids and/or phosphate acids are preferred for that purpose. For reasons of hazards to health and/or to the bone/tissue, their concentration should be limited. A particularly preferable acid, which is also considered as a mineral acid and which has a particularly positive effect on the overall target of killing and cleaning, is, on the other hand, carbonic acid. The usable quantity of the latter is, however, limited through its relatively low solubility in water.

Contrary thereto, organic acids, similar to mineral acids, provide pH-value-reducing and hydroxide-neutralizing $H^+$ ions. As, in addition, they do not produce any damages, or at most slight damages, in the tissue or in the patient as a whole, such organic acids are most particularly preferred as a basic constituent of the treatment liquid. Organic acids are, for example, alkane acids, fruit acids, carboxylic acids as well as hydroxy carbonic acids. $\alpha$-hydroxy carbonic acids have turned out to be particularly suitable acids. In particular, the particularly preferable acids lactic acid, citric acid, and malic acid have no effects hazardous to health on the patient in general or on the periimplantary tissue. Especially on implants greatly covered and contaminated with a biofilm, on which tartar has also developed, a good cleaning success was achieved with relatively low dosages of ethanoic acid. Other acids, which have the cleaning as well as the bactericidal effect, but, for health reasons, are not harmless, would be fumaric acid, gluconic acid, glycolic acid, salicylic acid, mandelic acid, tartaric acid, oxalic acid, and formic acid.

When the hydroxide ion $OH^-$ is neutralized with the corresponding $H^+$ ion of an acid, the metallic salt of the acid of the corresponding metal hydroxide will additionally be produced. The intended use of the acid is, therefore, not only advantageous for buffering the pH-value, but, in addition, contributes to the conversion of the relatively little water-soluble hydroxide into relatively well water-soluble salts, thus preventing the precipitation of unwanted deposits, detrimental to the process, on the component part needing treatment. The above-mentioned salts are in particular used when combining the above-mentioned preferred materials, among other, also in the field of medicine. During the neutralization of the potassium, sodium and/or calcium hydroxide with lactic acid, potassium lactate (possessing a broad-spectrum antimicrobial effect), sodium lactate or calcium lactate arises. It, however, the produced hydroxides are neutralized with citric acid, citrates of potassium, sodium or calcium will arise. Especially in the case of sodium citrate, this is particularly advantageous, as it prevents blood coagulation. This is particularly advantageous, because blood escaping during the process and coagulating on the implant surface might impede the ion wandering to the implant surface and, thus, the continuation of the treatment process as a whole.

Contrary thereto, in case of a neutralization of the hydroxides with malic acid, malates of the respective cation arise, which also have favorable effects on the process, in case of a neutralization of the hydroxides with ethanoic acid, acetates of potassium, sodium and/or calcium arise, which also have a favorable effect on the process.

Lactates, citrates, malates, and/or acetates of potassium, sodium and/or calciums all possess an acid-regulating effect and are so compatible that according to the present EU regulations concerning food additives, their use is not subject to any quantitative limitation.

When using acids in the electrolyte in combination with iodides and/or chlorides of sodium, potassium, magnesium, aluminium, and/or calcium, it has surprisingly turned out in the electrolytic application that the direct reduction of the $H^+$ ions influences the formation of bubbles so positively that the biofilm comes off clearly more quickly and better. At a high generation rate, a multitude of relatively small bubbles develop, which due to their relatively small size are able to detach the biofilm as a whole and not only locally from the surface underneath it. In this way, the biofilm is preferably detached as a whole or in relatively large coherent pieces instead of a multitude of smaller fragments, which entails a clearly improved cleaning effect.

Instead of metal cations, ammonium cations can also be used. In this case, there exists, however, the risk that in the electrolytic process, other ammonium compounds (e.g. ammonia) are generated. This constitutes a risk for the patient and is also perceived through a very disagreeable taste and smell.

It was observed in tests that the biofilm comes off partially in very small fragments or else in larger coherent pieces. The latter is preferred, because in this case, very favorable cleaning results can be achieved on relatively large areas. Examinations have also shown that the removal of the detached biofilm and/or its fragments is promoted by a formation of foam on the implant surface. It has turned out that it is favorable to apply, after the use of an electrolyte consisting of the above-described metal salts, acids and water, responsible in particular for killing and detaching, a second electrolyte, which shows in addition a formation of foam in the area of the cathode. Such a formation of foam can be achieved by preferably adding to the electrolyte another substance comprising at least three $CH_2$ chain links or at least one $CH_2$ chain link and at least one carbon ring compound. Here, e.g. oil and/or chlorhexidine can be used. Furthermore, ionic liquids, which preferably contain $I^-$, $Cl^-$ and/or $OH^-$ ions, can also be used. As the organic cation share of an ionic liquid is under certain circumstances reduced on the implant surface and remains there, it is possible in a particularly favorable embodiment, to add bone-growth factors to this cation share.

If chlorides and iodides are mixed in the correct ratio, the disturbing formation of chloric gas can be avoided. At the anode, the following is generated:

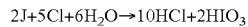

$$2J+5Cl+6H_2O \rightarrow 10HCl+2HIO_3$$

This means that both hydrochloric acid and iodic acid are formed at the anode. These acids certainly have a strong antimicrobial effect and are also neutralized again when meeting with the cathodically produced hydroxide.

A most particularly preferred composition of the treatment liquid, which in the laboratory test showed particularly favorable cleaning properties, comprises an aqueous solution of sodium iodide (NaI) or potassium iodide (KI) in a mixing ratio of at least 5 g, preferably at least 10 g, particularly preferably at least 20 g of the salt per 30 ml liquid (i.e. water $H_2O$, possibly enriched with $CO_2$), buffered, by the addition of lactic acid, to a pH-value of approx. 2.7 to 2.9.

In the process guidance, a mean current density at the post part 28 or at the component part needing treatment of at least 50 mA/cm$^2$, advantageously of at least 100 mA/cm$^2$, particularly preferably of at least 250 mA/cm$^2$, is provided, this current density being referred to the outer surface of the post part 28 (i.e. without taking into account any surface-enlarging properties, such as, for example roughness or surface structure). For the detachment of the biofilm, a mean current density of 50 mA/cm$^2$ to 300 mA/cm$^2$, advantageously of 100 mA/cm$^2$ to 200 mA/cm$^2$, has turned out to be particularly favorable. For the removal of the biofilm fragments, the mean current density should preferably be increased to the range of 300 mA/cm$^2$ to 5,000 mA/cm$^2$ or particularly advantageous of 1,000 mA/cm$^2$ to 2,000 mA/cm$^2$.

A particularly advantageous development of the system as a whole, i.e. of the electrolytic cleaning concept, additionally provides a charging of the treatment liquid with ultrasound. In this way, the cleaning effects can be assisted in a mechanical manner, in addition to their chemical principle, so that the achievable cleaning effect can clearly be enhanced. For this purpose, an ultrasound generator can be associated with the cleaning cannula in a suitable position.

In the embodiment shown in FIG. 2, the media cannula 2, on the one hand, and the conduction element 10, on the other hand, are designed as substantially independent component parts, which are electrically connected with the common supply unit 16. In the exemplary embodiment shown in FIG. 2, the conduction element 10 is designed in the manner of a "conventional" electrode, i.e. in particular as an electrically conductive needle-like element made of metal. Due to this design, the media cannula 2, on the one hand, and the conduction element 10, on the other hand, can be moved and positioned independently of each other, so that a particularly flexible handling of the component needing treatment is possible. In particular, the contact tip 14, on the one hand, and the outlet opening 4, on the other hand, can suitably be positioned independently of each other and, thus, possibly for an optimized electric contact with the component.

Contrary thereto, the exemplary embodiment according to FIG. 3 shows a variant, in which the media cannula 2 and the conduction element 10 are integrated into a common housing 30. In the exemplary embodiment shown, the media duct in the media cannula 2, on the one hand, and the electric conductor of the conduction element 10, on the other hand, are guided adjacent to each other and side by side, so that the contact tip 14 and the outlet opening 4 are positioned accordingly adjacent to each other at the free end 32 of the housing 30. Alternatively, a coaxial configuration of these components is also imaginable, in which the media duct in the media cannula 2 surrounds the conduction element 10 (or vice versa) in a ring-shaped manner. In general, an easier handling can be achieved through such an integrated construction with the common housing 30 for the media cannula 2 and the conduction element 10, because in this way, even a single-handed operation and positioning of the system is possible for the treating person.

The treatment system 1 and in particular its control unit 18 is designed for a coordinated process control in the sense that the feeding of the treatment liquid, on the one hand, and the charging with current, on the other hand, can be effected in a manner adapted to each other. For this purpose, it can, for example, be provided to effect via the control unit 18 a coordinated activation of the conveying unit for the treatment liquid, associated with the connection hose 6 or the reservoir 8, on the one hand, and the electric supply unit 16, on the other hand. This can be controlled automatically or, if necessary, also manually, via a switch. A manually operable switch can be arranged in particular in the area of the end piece of the cleaning cannula, so that the operator can access the system control while treating the patient.

For a particularly easy handling, the outlet opening 4 of the media cannula 2, as represented in the enlarged detail according to FIG. 4, is provided with a lock 40, which automatically opens when the outlet opening 4 is pressed against a surface with a force of more than a predefined minimum value. For this purpose, the lock 40 comprises in the exemplary embodiment according to FIG. 4 a hollow cylinder 42, mounted in the media cannula 2 so as to be shiftable in longitudinal direction of the media duct, whose cylindrical casing is provided with a multitude of inflow openings 44. The hollow cylinder 42 is supported by means of a prestressing spring 46 in such a way that in the unloaded state, it is positioned inside a guide sleeve 48 which is arranged in the area of the outlet opening 4 and which closes the inflow openings 44. If, however, the hollow cylinder 42 is pressed against a surface with a sufficiently high force of more than the spring force, it will be shifted inwards against the spring force into the media cannula 2, so that the inflow openings 44 will be freed and the medium can flow out from the media cannula 2 through the hollow cylinder 42. With such a construction or a similar one, it is achieved that the operator can directly control the discharge of the treatment liquid by pressing the media cannula against a contact surface.

In an advantageous development, this system is electrically coupled with the control unit 18 of the electric supply unit 16. In particular, a system design can be provided in which the shifting of the hollow cylinder 42, and thus the freeing of the outlet duct for the treatment liquid, is detected electrically, electronically or in a similar way and the corresponding signal is used as a triggering signal for the control unit 18. By means of this triggering signal, the energization of the component, for example in accordance with a stored energization pattern, can then be provided.

In addition, a swirler, a reflector or a diffusor 50 is associated with the outlet opening 4, in order to avoid that the electrolyte or the treatment liquid is pumped into the surrounding tissue at an excessively high pressure. If, namely, the electrolytic cleaning cannula is inserted between the implant and soft tissue, the flowing-in of the electrolyte into this pocket might cause an overpressure. To compensate this overpressure, the electrolytic media cannula 2 can additionally be provided on the outside with drain grooves or the like.

The electrolytic cleaning cannula or media cannula 2 can also be used for cleaning hip, knee, shoulder, elbow, foot, tow, hand, finger, vertebral-column implants and/or any other electrically conductive bone implants. The material of the exit of the electric current path is preferably a metal alloy or the same metal as the bone implant to be cleaned. These metals can be: titanium, zirconium, tantalum, and/or alloys of these or other metals, which are used for bone implants. The electric insulation of the two electrodes preferably consists of a biocompatible synthetic material, a glass or a ceramic.

The electric supply unit 16 and/or the control unit 18 associated therewith is suitably designed for the intended process control. This voltage or current supplied by it can be applied to the two electrodes as a direct voltage or current, with the polarity in both directions, or as an alternating voltage. If the voltage is an alternating voltage, it can have the shape of a sine, a triangle, a rectangle or any imaginable superimposition of these shapes, with different frequencies. Furthermore, this alternating voltage can be superimposed by a direct voltage. It is also possible to use a pulsating direct voltage.

As described above, it is particularly advantageous to feed several electrolytes differing from one another in composition either one after another or simultaneously to or onto the implant. The treatment system 1 is suitably configured for that purpose. In particular, several reservoirs 8 can be provided for at least two liquids or electrolytes, which can be conveyed into the media cannula 2 via pumps and via one or several valves or valve units simultaneously (mixingly) or one after another via the connection hose 6.

The electrodes may be made of the same material as the dental implant 20. As the dental implants 20 are preferably made of titanium or a titanium alloy, it is is preferred to make the other electrode(s) of another metal. Titanium and metals similar to titanium mostly form a protective oxide layer acting as an insulator when anodically energized. In order not to limit the current flow through such an oxide layer, in case of a cathodic energization of the dental implant 20, it is advantageous to use, as a counterelectrode, a metal which forms hardly any oxide layer or none at all. In a particularly favorable case, this electrode corrodes neither through contact with the media/electrolytes nor under application of a voltage or current. Preferably, this electrode is made of gold, platinum, palladium.

LIST OF REFERENCE NUMBERS

1 Treatment system
2 Media cannula
4 Outlet opening
6 Connection hose
8 Reservoir
10 Conduction element
12 End
14 Contact tip
16 Supply unit
18 Control unit
19 Cable
20 Dental implant
22 External thread
24 Space area
26 Jawbone
28 Post part
30 Housing
32 End
40 Lock
42 Hollow cylinder
44 Inflow opening
46 Prestressing spring
48 Guide sleeve
50 Diffusor

The invention claimed is:

1. A treatment system (1) for cleaning a component part contaminated with a biofilm, having a conduction element (10), which can be put into electric contact with the component needing treatment and which can be connected to a first pole of an electric supply unit (16), and having a media cannula (2) that supplies a treatment liquid and whose interior is connected in an electrically conductive manner with second pole of the electric supply unit (16), wherein media cannula (2) comprises an outlet opening (4) and a lock (40) whereby an inward shift of a hollow cylinder (42) into the media cannula (2) allows the treatment liquid to flow out from the media cannula (2) through the hollow cylinder (42).

2. The treatment system (1) of claim 1, wherein the conduction element (10) and the media cannula (2) are arranged in a common housing.

3. The treatment system (1) of claim 2, wherein, when the hollow cylinder (42) is positioned inside a guide sleeve (48) arranged in the area of the outlet opening (4), the treatment liquid is prevented from flowing from the media cannula (2).

4. The treatment system (1) of claim 3, wherein the hollow cylinder (42) is positioned inside the guide sleeve (48) in the absence of an exterior force that results in the inward shift.

5. The treatment system (1) of claim 1, wherein, when the hollow cylinder (42) is positioned inside a guide sleeve (48) arranged in the area of the outlet opening (4), the treatment liquid is prevented from flowing from the media cannula (2).

6. The treatment system (1) of claim 5, wherein the hollow cylinder (42) is positioned inside the guide sleeve (48) in the absence of an exterior force that results in the inward shift.

* * * * *